United States Patent [19]

Raths et al.

[11] Patent Number: 5,523,432
[45] Date of Patent: Jun. 4, 1996

[54] PROCESS FOR THE PRODUCTION OF QUATERNARY AMMONIUM SALTS OF FATTY ACID HYDROXYALKANESULFONIC ACIDS

[75] Inventors: Hans-Christian Raths, Monheim; Rainer Rueben, Duesseldorf; Manfred Biermann, Muelheim, all of Germany; Timothy J. Cassady, Hamilton, Ohio

[73] Assignee: Henkel Kommanditgesellschaft auf Aktien, Duesseldorf, Germany

[21] Appl. No.: 225,129

[22] Filed: Apr. 7, 1994

[51] Int. Cl.⁶ .................................................. C07C 309/00
[52] U.S. Cl. .................................. 554/92; 554/52; 554/94
[58] Field of Search ....................... 554/52, 92, 94

[56] References Cited

U.S. PATENT DOCUMENTS 3,151,136  9/1964  Kaczorowski et al. ................... 554/92

FOREIGN PATENT DOCUMENTS 0073626  3/1983  European Pat. Off. .

OTHER PUBLICATIONS

Happi, 18(3), 68 (1981).
Happi, Sep., 1984, 56.
Bull. Chem. Soc. Japan, 43, 2236–2240 (1970).

*Primary Examiner*—José G. Dees
*Assistant Examiner*—Deborah D. Carr
*Attorney, Agent, or Firm*—Wayne C. Jaeschke; John E. Drach; Daniel S. Ortiz

[57]  ABSTRACT

Quaternary ammonium salts of fatty acid hydroxyalkanesulfonic acids are made by reacting a hydroxyalkanesulfonic acid of the formula (I):

$$HO-(C_nH_{2n})-SO_3H \qquad (I):$$

wherein n=2 to 4 with a fatty acid having from 6 to 18 carbon atoms at a temperature range of from about 60° C. to about 120° C. and at a reduced pressure followed b reaction with an amine in an organic solvent.

9 Claims, No Drawings

PROCESS FOR THE PRODUCTION OF QUATERNARY AMMONIUM SALTS OF FATTY ACID HYDROXYALKANESULFONIC ACIDS

BACKGROUND OF THE INVENTION

1. Field of the Invention

This invention relates to a process for the production of quaternary ammonium salts of fatty acid hydroxyalkanesulfonic acids, in which a hydroxyalkanesulfonic acid is subjected to the condensation reaction with a $C_{6-18}$ fatty acid at elevated temperature and reduced pressure, any water of solution present and the water of reaction formed are directly removed from the reaction mixture and the fatty acid hydroxyalkanesulfonic acid is reacted with a base to form the corresponding quaternary ammonium salt of the fatty acid hydroxyalkanesulfonic acid. 2. Description of the Related Art Fatty acid hydroxyalkanesulfonic acid salts, more particularly fatty acid isethionates in the $C_{12-14}$ chain length range, are anionic surfactants with only minimal sensitivity to hardness, high foaming and wetting power and excellent compatibility with the skin. More particularly, they are distinguished by the fact that the skin can be cleansed without overly drying out. In addition, the soaps containing these compounds can even be used by people unable to tolerate typical high pH soaps. Accordingly, these compounds are used in cosmetic preparations and cleansing formulations Commercial fatty acid hydroxyalkanesulfonic acid salts are generally produced from the corresponding salt of hydroxyalkanesulfonic acid by reaction with the fatty acid in the presence of an esterification catalyst, for example ZnO, at temperatures of up to 250° C. However, dark-colored products are obtained in the production of ammonium fatty acid hydroxysulfonic acid salts by this process.

The fatty acid isethionates, particularly the sodium fatty acid isethionates frequently used, show only limited solubility in water which restricts their use to soaps, such as syndets and combination bars and opaque liquid formulations.

Quaternary ammonium salts of fatty acid hydroxyalkanesulfonic acids, more particularly ammonium fatty acid isethionate, are highly soluble in water and may be used in clear liquid formulations. However, this possibility is impaired by the fact that the quaternary ammonium salts of fatty acid isethionic acid prepared by conventional methods are dark in color so that, in the absence of bleaching, the liquid formulations containing them are also dark in color.

The problem addressed by the present invention was to provide a process for the production of quaternary ammonium salts of fatty acid hydroxyalkanesulfonic acids which would enable these compounds to be obtained in high yields and in light-colored highly concentrated form.

SUMMARY OF THE INVENTION

This invention relates to a process for making a quaternary ammonium salt of a fatty acid hydroxyalkanesulfonic acid comprising the steps of: (a) reacting a hydroxyalkanesulfonic acid of the formula (I):

$$HO-(C_nH_{2n})-SO_3H \qquad (I)$$

wherein n=2 to 4 with a fatty acid of the formula (II):

$$R^2COOH \qquad (II)$$

wherein $R^2CO$ is an aliphatic, linear or branched acyl radical having from 6 to 18 carbon atoms at a temperature range of from about 60° C. to about 120° C. and at a pressure sufficient to vaporize water at said temperature range to form a reaction mixture comprised of said fatty acid hydroxyalkanesulfonic acid while removing water from a reaction mixture; (b) dissolving said reaction mixture in an organic solvent; (c) forming a quaternary ammonium salt of said fatty acid hydroxyalkanesulfonic acid by reacting said reaction mixture with a base at a temperature of 18° C. to 35° C.

DESCRIPTION OF THE PREFERRED EMBODIMENTS

It has surprisingly been found that it is possible by the process according to the invention to produce high yields of quaternary ammonium salts of fatty acid hydroxyalkanesulfonic acids which are light in color. The process according to the invention may be carried out at considerably lower temperatures than known processes and without a catalyst.

In the process according to the invention, the hydroxyalkanesulfonic acid and the fatty acid are first subjected to the condensation reaction at temperatures of 60° to 120° C. and preferably at temperatures of 90° to 110° C. Any water of solution present and the water of reaction formed are directly distilled off. The molar ratio of fatty acid to hydroxyalkanesulfonic acid is in the range from 1.5:1 to 1:1.5 and preferably in the range from 1:1 to 1:1.2.

The condensation reaction is preferably carried out with no additional catalyst. The advantage of carrying out the reaction in this way is that there is no need for the removal of the catalyst from the reaction product otherwise necessary in condensation reactions and no catalyst residues are present in the reaction product.

The hydroxyalkanesulfonic acid used is preferably used in water-free form. Water present in the starting substances is distilled off at the beginning of the reaction. The hydroxyalkanesulfonic acid may readily be produced from its salts. It is preferably obtained from the sodium salt via acidic ion exchangers.

The fatty acid used as starting product corresponding to general formula (II) $R^2COOH$ is selected from caproic acid, oenanthic acid, caprylic acid, pelargonic acid, capric acid, undecanoic acid, undecenoic acid, lauric acid, lauroleic acid, tridecanoic acid, myristic acid, myristoleic acid, pentadecanoic acid, palmitic acid, palmitoleic acid, heptadecanoic acid, stearic acid, petroselic acid, petroselaidic acid, oleic acid, elaidic acid, linoleic acid, linolaidic acid, linolenic acid, elaeostearic acid and technical mixtures thereof. Fatty acids on a vegetable or animal basis, which may be completely or partly hydrogenated, are preferred. Mixtures of coconut oil fatty acid are particularly preferred.

The condensation reaction is carried out under a pressure under which water boils so that the water of reaction can readily be removed. A pressure in the range from about 2 to 100 mbar is preferred, water jet vacuum being particularly preferred.

The reaction mixture of hydroxyalkanesulfonic acid and fatty acid is heated in vacuo. The mixture should be heated only slowly because the reaction mixture can foam in vacuo at the beginning of the reaction. The beginning and end of the reaction are reflected in the formation of water of reaction. On completion of the reaction, the reaction mixture is kept at elevated temperature for about another 20 minutes to 1 hour to remove any water present. Removal of the water can be accelerated by addition to the reaction mixture of an organic solvent which forms a low-boiling azeotrope with water and which removes the water as an azeotrope from the reaction mixture.

The mixture is then dissolved in an inert organic solvent. Suitable solvents are any solvents with which the condensation product forms a homogeneous solution. Particularly suitable solvents are aliphatic and aromatic hydrocarbons, such as n-hexane, petroleum ether, isooctane; halogenated hydrocarbons, such as methylene chloride, chloroform or carbon tetrachloride; and alcohols, such as methanol, ethanol, n-propanol and i-propanol or mixtures thereof. Petroleum ether or a mixture of petroleum ether and i-propanol is preferably used.

The dissolved condensation product is reacted with a base at a temperature of 18° C. to 35° C. and preferably at a temperature of 20° C. to 27° C. The base may be used in the form of a pure substance or may be diluted with a corresponding solvent or inert gas. Suitable bases are, for example, ammonia, primary, secondary and tertiary (lower) alkylamines, in which lower alkyl is an alkyl containing 1 to 4 carbon atoms, or aminoalcohols, in which the alcohol is a lower alcohol containing 1 to 4 carbon atoms, and glucamine. Examples of suitable alkyl amines are monomethyl amine, monoethyl amine, monopropyl amine, monobutyl amine, dimethyl amine, diethyl amine, dipropyl amine, dibutyl amine, trimethyl amine, triethyl amine, tripropyl amine, tributyl amine. Examples of suitable alkanolamines are, for example, trimethanolamine, triethanolamine, tripropyl amine and tributyl amine.

The quaternary ammonium salt of the fatty acid hydroxyalkanesulfonic acid formed generally accumulates in the form of a white precipitate. On completion of the reaction, the reaction product is isolated in known manner. The solid product can normally be filtered off from the reaction mixture and subsequently washed with fresh solvent or solvent mixture several times, generally at least twice, and then dried in vacuo. If the product is soluble in the solvent, the solution obtained may be directly further processed or the product is obtained by distilling off the solvent.

The reaction according to the invention gives a white powder in a high yield of generally more than 90%.

The invention is illustrated by the following Example.

Example

About 57.9 g of isethionic acid (93%, 0.427 mole) and 85.53 g lauric acid (0.427 mole) were combined under nitrogen and heated in a water jet vacuum. The reaction actually began below 100° C. and was accompanied by gentle foaming. The main reaction was terminated after 1 h. The reaction mixture was kept at a maximum temperature of 120° C. for another 30 minutes.

11.8 g water and small quantities of lauric acid distilled over (theoretical: 11.6 g water). The resulting reaction mixture (131.6 g) was dissolved in 1.4 liters petroleum ether and ammonia was passed through with stirring at 25° C. The quaternary ammonium salt precipitating was washed three times with fresh petroleum ether and dried in a water jet vacuum. 135 g of a white powder were obtained. The product had the following composition:

approximately 91 to 93% of lauroyl isethionate $NH_4$ salt (determined by Epton titration of the anionic surfactant content)

approximately 2 to 3% of lauric acid $NH_4$ salt (determined by HPLC) and approximately 5 to 7% of ammonium isethionate (determined by HPLC).

After filtration and washing with the solvent, the product had a Klett color value of 49 (1 cm cuvette, 30% solution) whereas a commercial product had a Klett color value of 69 (1 cm cuvette, 30% solution).

What is claimed is:

1. A process for making a quaternary ammonium salt of a fatty acid hydroxyalkanesulfonic acid comprising the steps of: (a) reacting a hydroxyalkanesulfonic acid of the formula (I):

$$HO-(C_nH_{2n})-SO_3H \qquad (I)$$

wherein n=2 to 4 with a fatty acid of the formula (II):

$$R^2COOH \qquad (II)$$

wherein $R^2CO$ is an aliphatic, linear or branched acyl radical having from 6 to 18 carbon atoms at a temperature range of from about 60° C. to about 120° C. and at a pressure sufficient to vaporize water at said temperature range to form a reaction mixture comprised of said fatty acid hydroxyalkanesulfonic acid while simultaneously removing water from said reaction mixture; (b) dissolving said reaction mixture in an organic solvent; (c) forming a quaternary ammonium salt of said fatty acid hydroxyalkanesulfonic acid by reacting said reaction mixture with a base at a temperature of 18° C. to 35° C.

2. The process of claim 1 wherein said base is ammonia.

3. The process of claim 1 wherein step (a) is carried out at a temperature from about 90° to about 110° C.

4. The process of claim 1 wherein step (a) is carried out at a pressure of from about 2 to about 100 mbar.

5. The process of claim 1 wherein the base comprises at least one base selected from the group consisting of ammonia, primary lower alkylamines, secondary lower alkylamines, tertiary lower alkylamines, primary lower alkanolamines, secondary lower alkanolamines, tertiary lower alkanolamine and glucamine.

6. The process of claim 1 wherein the quaternary ammonium salt of the fatty acid hydroxyalkane sulfonic acid is not soluble in the organic solvent.

7. The process of claim 1 wherein the organic solvent comprises at least one organic solvent selected from the group consisting of aliphatic hydrocarbons, aromatic hydrocarbons, chlorinated hydrocarbons and alcohols.

8. The process of claim 5 wherein the quaternary ammonium salt of the fatty acid hydroxyalkane sulfonic acid is not soluble in the organic solvent.

9. The process of claim 5 wherein the organic solvent comprises at least one organic solvent selected from the group consisting of aliphatic hydrocarbons, aromatic hydrocarbons, chlorinated hydrocarbons and alcohols.

* * * * *